United States Patent [19]
Sagar et al.

[11] Patent Number: 4,960,413
[45] Date of Patent: Oct. 2, 1990

[54] WOUND DRESSING

[75] Inventors: Brian Sagar, Cheadle; Paul Hamlyn, East Didsbury; David Wales, Reddish, all of England

[73] Assignee: The Shirley Institute, Manchester, England

[21] Appl. No.: 309,971

[22] Filed: Feb. 13, 1989

Related U.S. Application Data

[63] Continuation of Ser. No. 51,454, May 19, 1987, abandoned.

[51] Int. Cl.$^5$ .............................. A61M 35/00
[52] U.S. Cl. ................................ 604/289; 128/156; 514/55
[58] Field of Search ............... 604/289, 304; 424/443–447; 128/156; 514/55, 779; 536/20

[56] References Cited

U.S. PATENT DOCUMENTS

| Number | Date | Inventor | Class |
|---|---|---|---|
| 2,040,880 | 5/1936 | Rigby | 264/186 |
| 2,459,897 | 1/1949 | Schwarz | 424/445 |
| 2,512,616 | 6/1950 | Eberl et al. | 128/156 |
| 2,688,586 | 9/1954 | Eberl et al. | 424/445 |
| 2,910,408 | 10/1959 | Pope et al. | 536/20 |
| 3,052,237 | 9/1962 | Chand | 128/156 |
| 3,196,075 | 7/1965 | Neuhauser | 128/156 |
| 3,533,940 | 10/1970 | Peniston et al. | 210/728 |
| 3,879,168 | 4/1975 | Franklin et al. | 128/156 |
| 3,903,268 | 9/1975 | Balassa | 128/156 |
| 4,363,319 | 12/1982 | Altshuler | 128/156 |
| 4,373,519 | 2/1983 | Errede et al. | 128/156 |
| 4,391,799 | 7/1983 | Mason Jr. et al. | 514/779 |
| 4,421,583 | 12/1983 | Aldred et al. | 128/156 |
| 4,524,064 | 6/1985 | Nambur | 514/779 |
| 4,532,134 | 7/1985 | Malette et al. | 128/334 R |
| 4,562,110 | 12/1985 | Tong | 128/156 |
| 4,570,629 | 2/1986 | Widra | 128/156 |
| 4,572,906 | 2/1986 | Sparkes et al. | 424/444 |
| 4,651,725 | 3/1987 | Kifive et al. | 128/156 |
| 4,659,700 | 4/1987 | Jackson | 514/55 |
| 4,699,135 | 10/1987 | Motosugi et al. | 128/156 |

FOREIGN PATENT DOCUMENTS 199531 10/1986 European Pat. Off. .
200574 11/1986 European Pat. Off. .

OTHER PUBLICATIONS

"Innovations that Enrich the Material World"—Laboratory News 3, Oct. 1988.
"Production and Isolation of Chitosan from *Mucor rouzii*", Applied and Environmental Microbiology, Aug. 1979, pp. 323–328.

*Primary Examiner*—C. Fred Rosenbaum
*Assistant Examiner*—Sharon Rose
*Attorney, Agent, or Firm*—Oblon, Spivak, McClelland, Maier & Neustadt

[57] ABSTRACT

There is disclosed a wound dressing comprised by an assembly of microfungal fibres which have been treated with alkali to expose chitin and chitosan. The fibres may be derived from hyphae or from sporangiophores. The assembly may include other fibres, may be bleached and incorporate other additives such as silver as an anti-bacterial agent.

13 Claims, 1 Drawing Sheet

WOUND DRESSING

This application is a continuation of application Ser. No. 07/051,454, filed on May 19, 1987, now abandoned.

This invention concerns a wound dressing.

The wound healing properties of chitin and chitin derivatives have long been recognized and documented. Present practice suggests that wounds should be kept moist to prevent scabbing, reduce the development of scar tissue and minimise healing time.

The extraction of chitin from its natural sources and its incorporation in conventional wound dressings is quite costly.

It is an object of the present invention to provide an improved wound dressing adapted to current medical practice and at economic cost.

According to the present invention there is provided a wound dressing comprised by an assembly of microfungal fibres which have been treated with alkali to expose chitin and chitosan.

The microfungal fibres may be hyphae or sporangiophores.

The microfungal hyphae may be Mucor mucedo or Rhizomucor miehei.

The assembly may be a wet-laid non woven mat which may incorporate a plasticiser.

The plasticiser may be water or may be glycerol or polyethylene glycol.

When water is the plasticiser the wet-laid mat may be cut to size and sealed in a water vapour impermeable pack without being allowed to dry.

The assembly may be an absorbed freeze-dried pad.

The assembly or the fibres from which it is formed may be bleached.

The assembly may incorporate other fibres of substances known to assist or facilitate wound healing, such as of collagen, a well-known haemostatic agent or of an alginate, useful as a physical barrier to prevent drying and adhesion between the wound and the dressing material. The assembly may also incorporate bound metallic silver, useful as an anti-bacterial agent.

The wound dressings may be treated with a bi-functional cross-linking agent such as glutaraldehyde to improve their strength.

The invention will be further apparent from the following description which concerns by way of example only the preparation of various forms of wound dressing embodying same and with reference to the accompanying drawings, in which.

Figure 1:
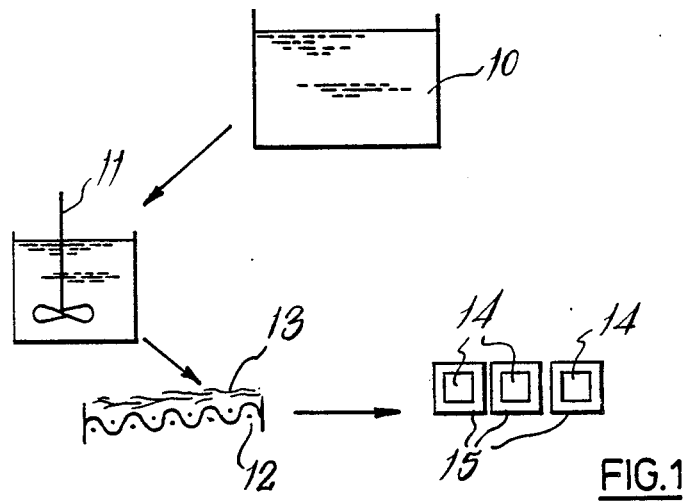
FIG. 1 is a diagrammatic illustration of a batch process for preparing a first form of wound dressing.

Referring firstly to FIG. 1, micro-fungal mycelia are produced from a culture of Mucor mucedo (CMI 184 726), grown in a nutrient solution containing malt extract (17q/1) and mycological peptone (3g/1) in a fermenter vessel 10 at a temperature of 30° C. for one to two days.

The culture is then washed and treated with a 2N boiling solution of sodium hydroxide for one hour to dissolve protein from the outer layers of the cell walls and expose the underlying chitin and chitosan. Further de-acetylisation of the chitin may be effected by 40% sodium hydroxide solution.

The culture is repeatedly washed until neutral pH is obtained and then bleached by treatment with a solution of hydrogen peroxide (80 ml/1 37% $H_2O_2$ + 40 g/1 NaOH + 40 g/1 sodium silicate) for two hours at room temperature.

The culture is washed again and disintegrated using normal paper making equipment 11 to ensure an even dispersion of the hyphae in water to form a slurry. The slurry is strained through a filter medium 12 to leave a wet-laid matt 13 having a thickness of 1 mm or thereabouts.

If desired other fibres having wound healing properties such as of collagen or an alginate or both may be mixed with the hyphae before the matt is laid, as may textile fibres to give mechanical strength or other properties.

Suitably sized portions 14 for wound dressings of desired size are cut from the matt 13 and immediately encapsulated whilst still wet in airtight packs 15 and subsequently sterilised. The retained water acts as a plasticiser to prevent the hyphae from becoming dry and brittle and also ensures that the dressings are moist when removed from the packs for use.

Alternatively glycerol or polyethylene glycol may be added to the slurry before the matt is laid.

In another example Mucor mucedo is replaced by Rhizomucor miehei (CMI 147 066) which is fermented at 50° C.

In yet another example sporangiophores of Phycomyces blakesleeanus (CBS 283 35) are grown in static culture, harvested and introduced to the vessel 10 for the alkali and subsequent treatments.

Figure 2:
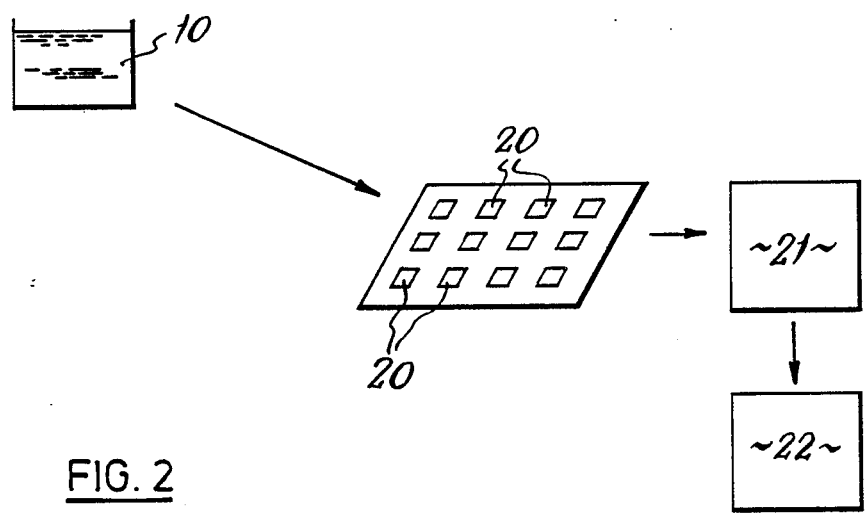
FIG. 2 is a diagrammatic illustration of a batch process for making a second form of wound dressing.

As shown in FIG. 2, the slurry from vessel 10 may be poured in to shaped moulds or dishes 20 which are then frozen in a deep freezer 21 for say sixteen hours and then freeze-dried for twenty-eight hours in a freeze-drier 22. Absorbent pads typically of say 10 cms in diameter or larger and from a few millimeters to several centimeters thick can be produced in this way.

Figure 3:
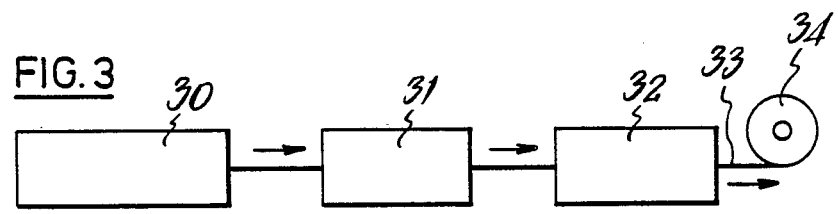
FIG. 3 is a diagrammatic illustration of a continuous process for making the second form of wound dressing.

FIG. 3 illustrates a continuous process for producing a web in which the slurry is laid down using conventional paper making machinery 30 and passed straight into a continuous freezer 31 and from there into a continuous freeze drying plant 32 after which the resulting matt 33 can be rolled up as at 34.

It is surprising that the matt is so flexible and strong as to permit this since, previously, 100% fungal matts have been brittle unless plasticiser has been added.

Use of a plasticiser in freeze-dried wound dressings is not necessary but a plasticiser may of course be added if desired.

It will be appreciated that it is not intended to limit the invention to the above example only, many variations, such as might readily occur to one skilled in the art, being possible, without departing from the scope thereof as defined by the appended claims.

Thus for example, the matts or pads or fibres from which they are formed may be treated in a solution of silver nitrate whereby silver ions will be captured by the chitosan and thus be present in the dressings as an anti-bacterial agent.

Again for example, the dressings may be treated with a bi-functional cross-linking agent such as glutaraldehyde.

Yet again, for example the wet-laid matts may be laminated with one or more backing layers of conventional, textile fibre if desired.

Tests carried out by Royal National Orthopaedic Hospital at Stamore Middlesex, indicated that wound dressings prepared in accordance with the invention from Mucor mucedo gave encouraging results in terms of the quality and quantity of repair tissue.

We claim:

1. A wound dressing comprising an assembly of microfungal fibers which have been treated with alkali to dissolve protein from the outer layers of the cell walls and expose chitin and chitosan.

2. A wound dressing according to claim 1 wherein the microfungal fibers are hyphae.

3. A wound dressing according to claim 1 wherein the microfungal fibers are sporangiophores.

4. A wound dressing according to claim 1 wherein the assembly is a wet-laid mat.

5. A wound dressing according to claim 4 wherein the wet-laid mat includes a plasticiser.

6. A wound dressing according to claim 5 wherein said plasticiser is water.

7. A wound dressing according to claim 1 wherein the assembly is frozen and freeze-dried.

8. A wound dressing according to claim 1 wherein the assembly is cut to a desired size and sealed in a water vapour impermeable pack.

9. A wound dressing according to claim 1 wherein the microfungal fibers are bleached.

10. A wound dressing according to claim 1 wherein other fibers are included with the microfungal fibres.

11. A wound dressing according to claim 1 wherein the alkali treated fibers are treated with a silver salt whereby silver ions are captured and present in the dressing as an anti-bacterial agent.

12. A wound dressing according to claim 1 wherein the assembly is treated with a bi-functional cross-linking agent.

13. A wound dressing according to claim 1 wherein the assembly is laminated with one or more backing layers of conventional textile material.

* * * * *